United States Patent
Baudino

(10) Patent No.: US 10,716,531 B2
(45) Date of Patent: Jul. 21, 2020

(54) EQUIPMENT COMPRISING AN ACOUSTIC MEASUREMENT DEVICE COMPRISING MEANS FOR LINKING A SENSOR TO A RIGID STRUCTURE

(71) Applicant: H4D, Aix-en-Provence (FR)

(72) Inventor: Franck Baudino, Neuilly sur Seine (FR)

(73) Assignee: H4D, Aix-en-Provence (FR)

( * ) Notice: Subject to any disclaimer, the term of this patent is extended or adjusted under 35 U.S.C. 154(b) by 517 days.

(21) Appl. No.: 15/326,867

(22) PCT Filed: Jul. 16, 2015

(86) PCT No.: PCT/EP2015/066319
§ 371 (c)(1),
(2) Date: Mar. 20, 2017

(87) PCT Pub. No.: WO2016/008996
PCT Pub. Date: Jan. 21, 2016

(65) Prior Publication Data
US 2017/0202535 A1    Jul. 20, 2017

(30) Foreign Application Priority Data
Jul. 18, 2014 (FR) ..................... 14 56984

(51) Int. Cl.
*A61B 5/00* (2006.01)
*A61B 7/02* (2006.01)
(Continued)

(52) U.S. Cl.
CPC ............... *A61B 7/02* (2013.01); *A61B 7/00* (2013.01); *A61B 5/6802* (2013.01); *A61B 7/04* (2013.01)

(58) Field of Classification Search
CPC ..... A61B 7/02; A61B 7/04; A61B 2562/0204; A61B 5/6802; A61B 5/6813; A61B 5/6831; A61B 5/6844
See application file for complete search history.

(56) References Cited

U.S. PATENT DOCUMENTS 6,878,117 B1 * 4/2005 Watrous ............... A61B 7/00
128/903
2002/0038089 A1   3/2002 Watrous
(Continued)

FOREIGN PATENT DOCUMENTS

GB    1219618    1/1971
TW     453866    9/2001

OTHER PUBLICATIONS

International Search Report issued in the International Application No. PCT/EP2015/066319 dated Oct. 30, 2015 (7 pages).
(Continued)

*Primary Examiner* — Max F Hindenburg
(74) *Attorney, Agent, or Firm* — Hamre, Schumann, Mueller & Larson, P.C.

(57) ABSTRACT

The invention relates essentially to equipment (100) to be positioned against the body of a subject, said equipment including an acoustic measurement device (105) having at least one acoustic sensor (110) for measuring acoustic signals given off by the subject's body, wherein said measurement device (105) further comprises:
a rigid structure (120) that is stationary relative to the equipment; and
connection means (450, 550, 650, 750, 850, 950) for connecting the acoustic sensor (110) to the rigid structure (120);
the connection means (450, 550, 650, 750, 850, 950) and the acoustic sensor (110) being movable relative to the rigid structure (120), and the connection means (**450, 550, 650, (Continued)

750, 850, 950) defining predetermined degrees of freedom of movement for the acoustic sensor (110).

18 Claims, 6 Drawing Sheets

(51) Int. Cl.
*A61B 7/00* (2006.01)
*A61B 7/04* (2006.01)

(56) References Cited

U.S. PATENT DOCUMENTS

| | | | |
|---|---|---|---|
| 2008/0139893 A1* | 6/2008 | Lee | A61B 7/04 600/300 |
| 2009/0030298 A1 | 1/2009 | Matthews et al. | |
| 2010/0056956 A1* | 3/2010 | Dufresne | A61B 7/04 600/586 |
| 2014/0095196 A1 | 4/2014 | Waterson et al. | |

OTHER PUBLICATIONS

Written Opinion issued in the International Application No. PCT/EP2015/066319 dated Oct. 30, 2015 (6 pages).
Office Action issued for counterpart Chinese Patent Application No. 201580050588.4, dated May 30, 2019, 12 pages including English translation.

\* cited by examiner

EQUIPMENT COMPRISING AN ACOUSTIC MEASUREMENT DEVICE COMPRISING MEANS FOR LINKING A SENSOR TO A RIGID STRUCTURE

BACKGROUND OF THE INVENTION

The present invention relates to the field of acoustic measurements.

More precisely, the present invention relates to the field of equipment including an acoustic measurement device, the equipment being to be positioned against the body of a subject.

In known manner, medical equipment may include an acoustic measurement device having a plurality of acoustic sensors.

Document US 2008/0139893 discloses a vest having a measurement device with a plurality of acoustic sensors. The acoustic sensors are positioned in a line, on one of the faces of the vest, and by way of example they are interposed between two layers of flexible material of the vest. The acoustic sensors may also be positioned on rigid elements that are assembled to one another in movable manner. Thus, when a user puts on the vest, the acoustic sensors can be positioned against the user's body as a result of a pleating of the vest.

Nevertheless, those sensors are not suitable for taking optimum acoustic measurements.

One of the objects of the invention is to solve such a problem.

OBJECT AND SUMMARY OF THE INVENTION

To this end, the present invention relates to an equipment to be positioned against the body of a subject, said equipment including an acoustic measurement device having at least one acoustic sensor for measuring acoustic signals given off by the subject's body, wherein said measurement device further comprises:

a rigid structure that is stationary relative to the equipment; and connection means for connecting the acoustic sensor to the rigid structure;

the connection means and the acoustic sensor being movable relative to the rigid structure, and the connection means defining predetermined degrees of freedom of movement for the acoustic sensor.

The invention is advantageous in that the movement of the acoustic sensors is controlled within predetermined degrees of freedom defined by the connection means. Unlike the flexible material or the rigid elements of the prior art vest that do not enable the acoustic sensors to move under control, the combination of the rigid structure and the movable connection means enables the acoustic sensor to be oriented accurately against the body of the user. This combination thus ensures great accuracy for the movement of the acoustic sensor.

In a particular embodiment, the rigid structure includes an orifice passing an element connected to the acoustic sensor in such a manner that the acoustic sensor is positioned outside the rigid structure.

This arrangement thus enables the acoustic sensor to be oriented accurately against the user's body, while nevertheless being strong.

In a particular embodiment, the element connected to the acoustic sensor is a transmission cable.

In a particular embodiment, the element connected to the acoustic sensor is a rod.

In a particular embodiment, for at least one predetermined degree of freedom, the movement of the acoustic sensor is limited by the surface of the rigid structure.

In a particular embodiment, the movement of the acoustic sensor is limited in rotation by a predetermined angle relative to the surface of the rigid structure and/or in translation along a predetermined linear shift towards the rigid structure.

In a particular embodiment, the connection means enable the acoustic sensor to pressure on the subject's body when the equipment is positioned against the subject's body.

In normal situations of use of the equipment, this pressure serves to guarantee continuous contact between the acoustic sensor and the subject's body.

In a particular embodiment, the connection means comprise:

a ball support fastened to the rigid structure; and a ball connected to the acoustic sensor and positioned inside the ball support.

The acoustic sensor can thus move in rotation relative to the rigid structure with three degrees of freedom in rotation, this rotation being limited for two degrees of freedom in rotation by the surface of the rigid structure.

In a particular embodiment, the connection means comprise:

a spring having a first end positioned against the rigid structure and a second end fastened to the acoustic sensor.

Thus, the acoustic sensor can move in translation relative to the rigid structure along an axis perpendicular to the surface of the acoustic sensor, this movement in translation being limited by the surface of the rigid structure.

In a particular embodiment, the connection means comprise:

a spring having a first end and a second end;

a ball support; and a ball positioned inside the ball support.

In a particular embodiment:

the ball is fastened to the acoustic sensor;

the first end of the spring is fastened to the rigid structure; and the second end of the spring is fastened to the ball support.

Thus, the acoustic sensor can move in rotation relative to the rigid structure with three degrees of freedom in rotation, this movement in rotation being limited for two degrees of freedom in rotation by the rigid structure, and/or can move in translation relative to the rigid structure along an axis perpendicular to the surface of the acoustic sensor, this movement in translation being limited by the surface of the rigid structure.

In a particular embodiment:

the ball has an orifice passing the element connected to the acoustic sensor;

the ball support is fastened to the rigid structure;

the first end of the spring is fastened to the rigid structure; and the second end of the spring is fastened to the element connected to the acoustic sensor.

In a particular embodiment:

the acoustic sensor is connected to a transmission cable;

the rigid structure includes an orifice passing the transmission cable;

the ball includes an orifice passing the transmission cable;

the ball support is fastened to the rigid structure;

the first end of the spring is fastened to the rigid structure; and the second end of the spring is fastened to the transmission cable.

Thus, the acoustic sensor can move in rotation relative to the rigid structure with three degrees of freedom in rotation, this movement in rotation being limited for two degrees of freedom in rotation by the rigid structure, and/or can move in translation relative to the rigid structure along an axis perpendicular to the surface of the acoustic sensor, this movement in translation being limited by the surface of the rigid structure.

In a particular embodiment, the connection means comprise a bellows positioned between the acoustic sensor and the rigid structure.

Thus, the acoustic sensor can move in rotation relative to the rigid structure with three degrees of freedom in rotation, this movement in rotation being limited for two degrees of freedom in rotation by the rigid structure, and/or it can move in translation relative to the rigid structure along an axis perpendicular to the surface of the acoustic sensor, this movement in translation being limited by the surface of the rigid structure.

In a particular embodiment, the connection means comprise:
   a spring having a first end connected to the acoustic sensor and a second end connected to the rigid structure; and
   a flexible protective membrane extending between the acoustic sensor and the rigid structure.

Thus, the acoustic sensor can move in rotation relative to the rigid structure with three degrees of freedom in rotation, this movement in rotation being limited for two degrees of freedom in rotation by the rigid structure, and/or it can move in translation relative to the rigid structure along an axis perpendicular to the surface of the acoustic sensor, this movement in translation being limited by the surface of the rigid structure.

In a particular embodiment, the equipment further includes shield means positioned around the acoustic sensor.

These shield means serve to shield the measurement zone of the acoustic sensor from the outside environment, and thus enable measurements to be taken that incorporate a minimum amount of outside disturbance.

In a particular embodiment, the acoustic sensor is a stethoscope chestpiece.

In a particular embodiment, the equipment is in the form of a seat, a belt, or a vest.

In a particular embodiment, the equipment is in the form of a seat cover, or a harness.

The invention also provides a health booth including equipment as defined above.

BRIEF DESCRIPTION OF THE DRAWINGS

Other characteristics and advantages of the present invention appear from the following description made with reference to the accompanying drawings, which show an embodiment having no limiting character. In the FIGS..

DETAILED DESCRIPTION OF EMBODIMENTS

Figure 1:
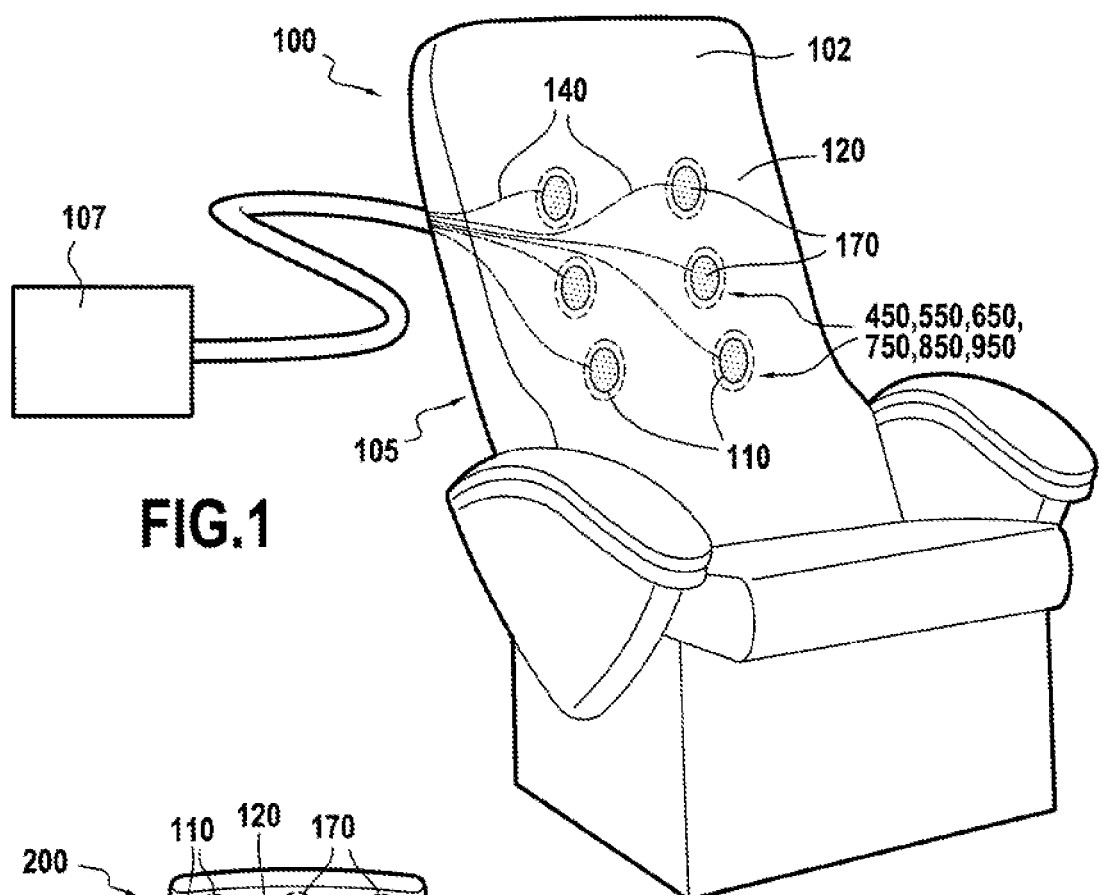
FIGS. 1 to 3 and 10 to 14 schematically represent equipment in accordance with embodiments of the invention.

FIGS. 1 to 3 and 10 to 14 schematically represent equipment 100, 200, 300, 1000, 1100 to be positioned against a subject's body. The equipment 100, 200, 300, 1000, 1100 comprises an acoustic measurement device 105 having at least one acoustic sensor 110 for measuring acoustic signals given off by the subject's body.

Furthermore, the acoustic measurement device 105 has a rigid structure 120 that is stationary relative to the equipment 100, 200, 300, 1000, 1100. The acoustic measurement device 105 also has connection means 450, 550, 650, 750, 850, 950 for connecting the acoustic sensor 110 to the rigid structure 120.

The connection means 450, 550, 650, 750, 850, 950 and the acoustic sensor 110 are movable relative to the rigid structure 120. Furthermore, the connection means 450, 550, 650, 750, 850, 950 define predetermined degrees of freedom for movement of the acoustic sensor 110.

The movement of the acoustic sensor 110 is limited for at least one predetermined degree of freedom by the surface of the rigid structure 120. More precisely, the movement of the acoustic sensor 110 is limited to move in rotation to a predetermined angle relative to the surface of the rigid structure 120 and/or to move in translation with a predetermined linear shift towards the rigid structure 120.

As shown in the FIGS., the acoustic sensor 110 is positioned outside the rigid structure 120. The movement of the acoustic sensor 110 is thus limited, for at least one degree of freedom, by the outside surface of the rigid structure 120. The term "outside" means "facing towards the outside".

The acoustic sensor 110 may be connected to signal processing means 107 via a transmission cable 140. In an example, the acoustic sensor 110 is a stethoscope chestpiece. Furthermore, in an example, the rigid structure 120 is covered by a flexible and elastic textile cloth.

As shown in FIGS. 4 to 9, the rigid structure 120 may include an orifice 422 through which the transmission cable 140 passes, so that the acoustic sensor 110 is positioned outside the rigid structure 120.

This arrangement of the acoustic sensor 110 relative to the rigid structure 120 makes it possible to orient the acoustic sensor 120 accurately against the user's body while still being strong.

In a variant, the acoustic sensor 110 is a wireless sensor, and it communicates with the signal processing means 107 via a wireless communication interface. The acoustic sensor 110 can then be connected to a rod, this rod passing through an orifice 422.

In an example, the outside surface of the rigid structure 120 is plane between two orifices 422.

In an example, shield means 170 extend over the outside wall of the acoustic sensor 110. These shield means 170 serve to shield the measurement zone from the outside environment, and thus make it possible to ensure that measurements taken incorporate a minimum amount of external disturbance.

More precisely, FIG. 1 schematically represents a first embodiment of equipment 100 in the form of a seat. In this first embodiment, the acoustic measurement device 105 may have six acoustic sensors 110. In a variant, the acoustic measurement device 105 has some other number of acoustic sensors 110.

The seat 100 has a back 102 in which the rigid structure 120 of the acoustic measurement device 105 is positioned. The acoustic sensors 110 are arranged at the surface of a portion of the back 102 that can come into contact with the back of a user. Thus, when a user sits on the seat 100 and leans against the back 102, the user's back exerts pressure on the acoustic sensors 110.

In a variant, the acoustic measurement device 105 includes a cushion positioned against the back 102, with the acoustic measurement device 105 being positioned in the cushion. The acoustic sensors 110 are then arranged at the surface of a portion of the cushion that can come into contact with a user's back.

Figure 10:
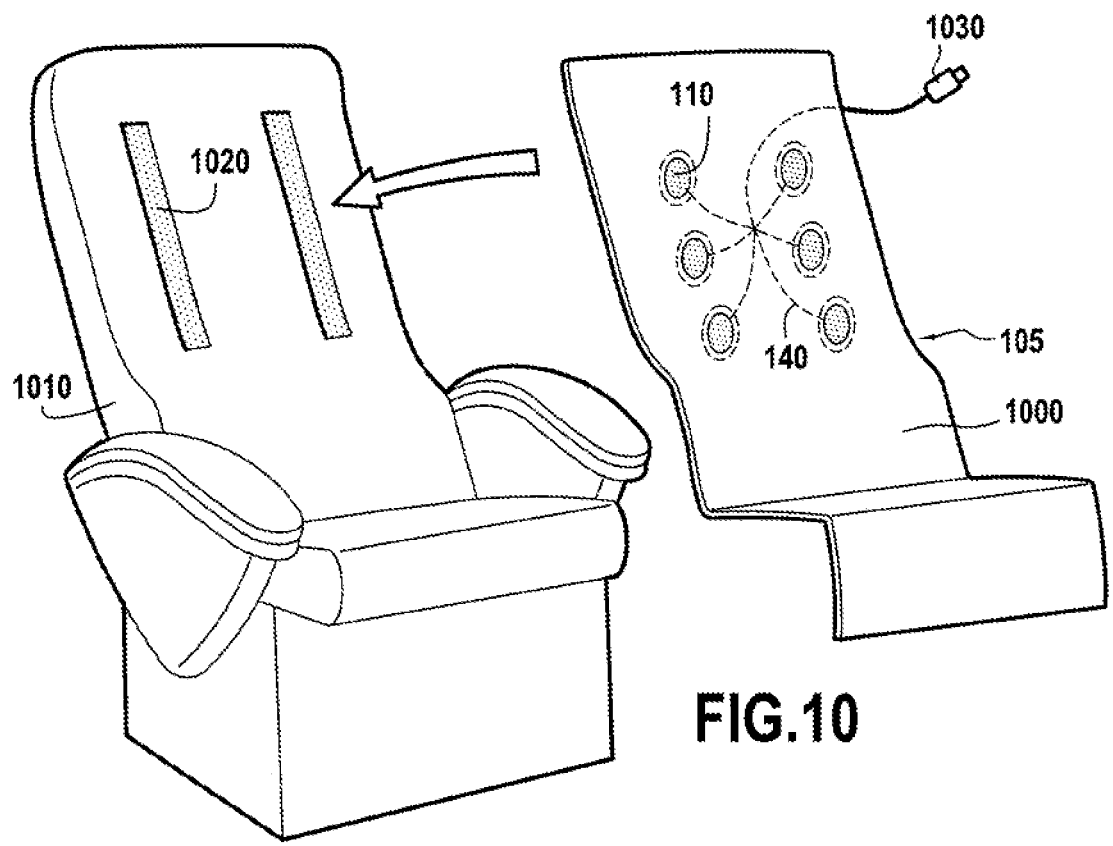

In another variant shown in FIG. 10, the equipment is in the form of a seat cover 1000 suitable for fastening to a seat 1010 by fastener means 1020. In an example, the fastener means 1020 are in the form of one or more self-adhesive strips. In addition, the outside structure of the seat cover 1000 may be a sheet, a fabric, a piece of leather, or a semi-rigid shell. The acoustic sensors 110 may be connected to the signal processing means 107 via their respective transmission cables 140 and a connection cable 1030 having a universal serial bus (USB) or jack type plug.

Figure 2:
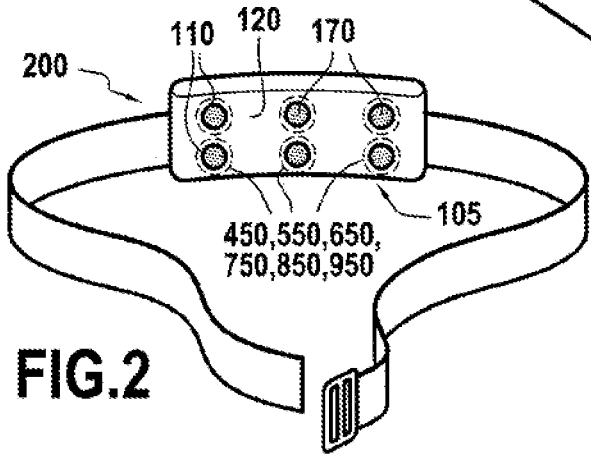

Furthermore, FIG. 2 schematically represents a second embodiment of equipment 200 in the form of a belt. In this second embodiment, the acoustic measurement device 105 may have six acoustic sensors 110. In a variant, the acoustic measurement device 105 may have some other number of acoustic sensors 110.

The acoustic sensors 110 are arranged at the surface of a portion of the belt that faces towards the user while the belt is in use, this portion being suitable for coming into contact with a user's back or chest. Thus, when the belt is positioned around the user, the user's back or chest exerts pressure against the acoustic sensors 110.

In an example, the material of the outside structure of the belt 200 is of the neoprene type.

Figure 14:
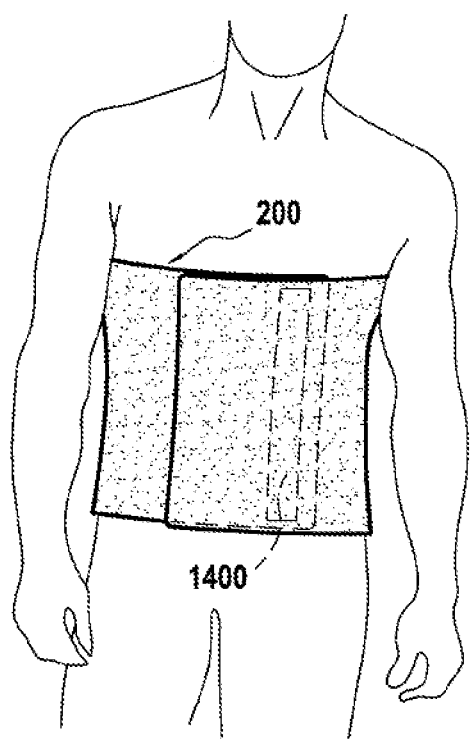

In an element shown in FIG. 14, the belt 200 is a dorsal belt having attachment means 1400 that may comprise one or more self-adhesive strips.

Figure 3:
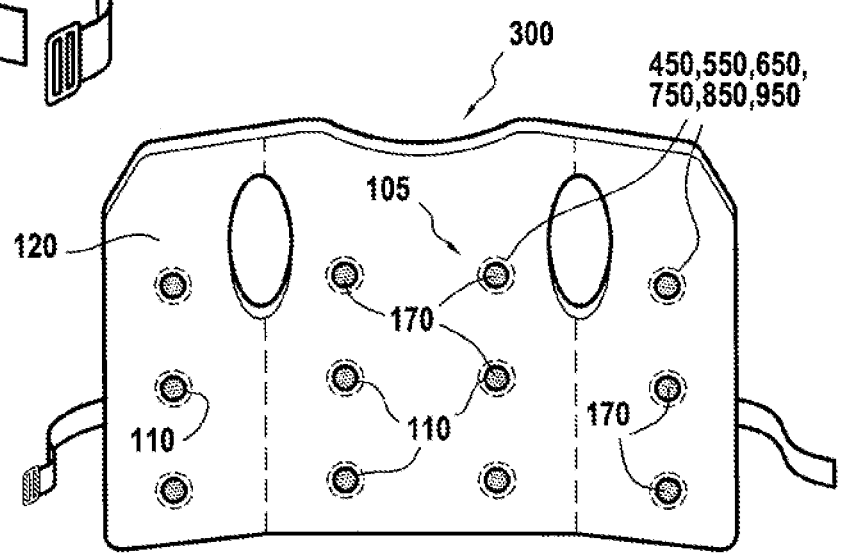

Furthermore, FIG. 3 schematically represents a third embodiment of equipment 300 in the form of a vest. In this third embodiment, the acoustic measurement device 105 may have twelve acoustic sensors 110. Six acoustic sensors 110 may be arranged at the surface of the rear inside portion of the vest, which portion may be in contact with the user's back. Furthermore, six other acoustic sensors may be arranged at the surface of the front inside portion of the vest, this portion being suitable for coming into contact with the user's chest. In a variant, the acoustic measurement device 105 could have some other number of acoustic sensors 110. In a variant, the acoustic sensors 110 are arranged at the surface of the rear inside portion of the vest. In a variant, the acoustic sensors 110 are arranged at the surface of the front inside portion of the vest.

When the vest is in position on the user, the user's back and/or chest exerts pressure against the acoustic sensors 110.

Figure 13:
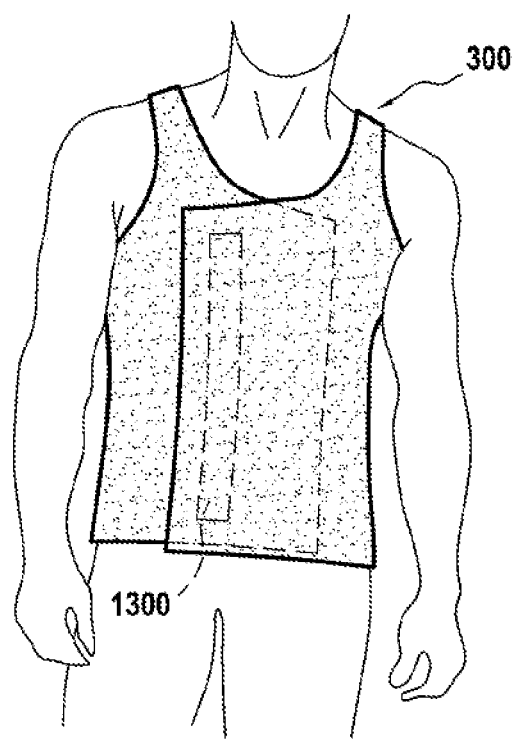

In the example shown in FIG. 13, the vest 300 has a closure 1300, possibly in the form of at least one self-adhesive strip.

Figures 11, 12:
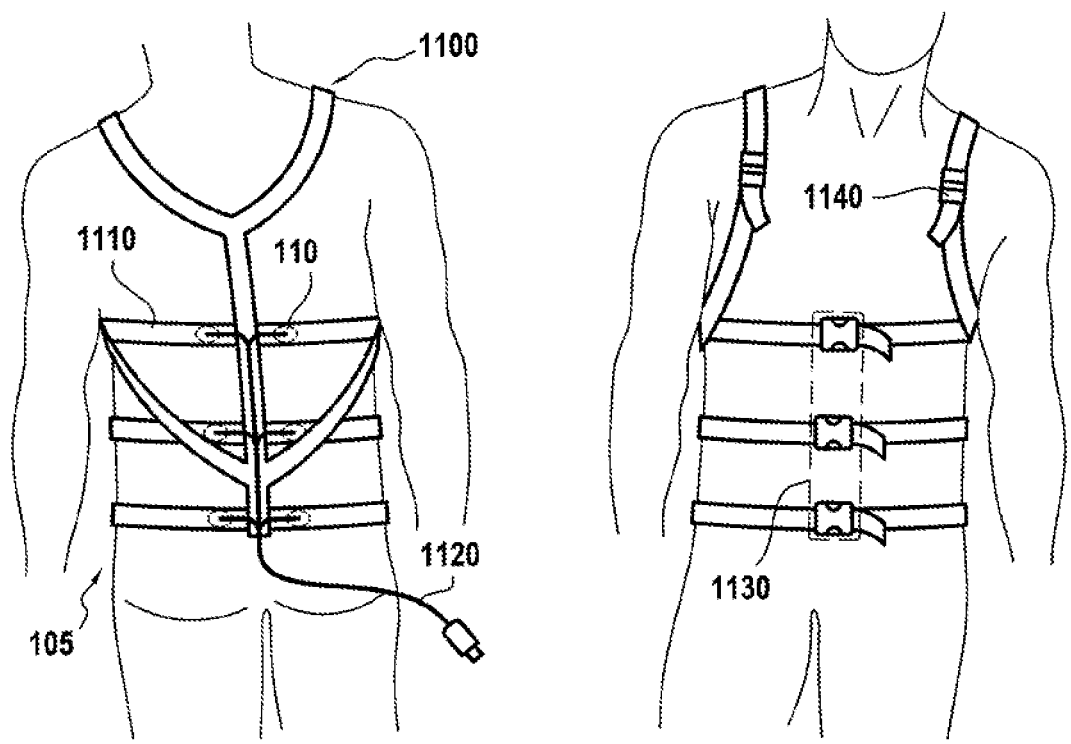

FIGS. 11 and 12 schematically represent a fourth embodiment of the invention, where the equipment 110 is in the form of a harness made up of straps 1100. As shown in FIG. 11, in this fourth embodiment, the acoustic measurement device 105 may have six acoustic sensors 110, positioned at the back of the harness so as to come into contact with the user's back.

The acoustic sensors 110 may be connected to the signal processing means 107 via respective transmission cables 140, and a connection cable 1120 of the USB or jack plug type.

Furthermore, in an example, the harness 1100 has a closure 1130 that may be in the form of a female buckle suitable for receiving a plurality of male buckles, or at least one female buckle and an associated male buckle. The harness 1100 may also include adjustment buckles 1140.

FIGS. 4 to 9 show variants of connection means that can be arranged in the equipment of FIGS. 1 to 3, and 10 to 14.

Figure 4:
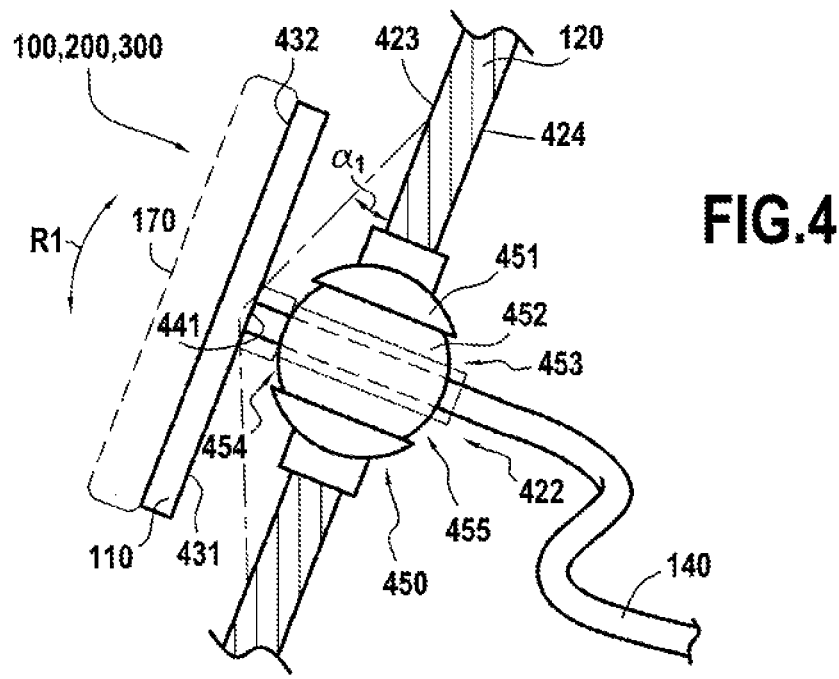
FIGS. 4 to 9 schematically represent variants of connection means for equipment in accordance with embodiments of the invention.

FIG. 4 schematically represents an acoustic sensor 110 connected to the rigid structure 120 via a first variant of the connection means 450 for the equipment 100, 200, 300, 1000, 1100 of the first, second, third, or fourth embodiment.

More precisely, the acoustic sensor 110 has an inside wall 431 facing the rigid structure 120 and an outside wall 432 facing the other way. The transmission cable 140 has a first end 441 connected to the inside wall 431 of the acoustic sensor 110.

Furthermore, the rigid structure 120 includes an orifice 422. This orifice 422 passes the transmission cable 140 so that the acoustic sensor 110 is positioned outside the rigid structure 120. The rigid structure 120 also has an outside wall 423 facing towards the acoustic sensor 110 and an inside wall 424 facing the other way.

The connection means 450 comprise a ball 452 and a ball support 451.

More precisely, the ball support 451 is fastened to the wall of the orifice 422 of the rigid structure 120. By way of example, the ball support 451 is in the form of a hollow sphere with a through orifice 453. This orifice 453 has an outside end 454 facing towards the outside of the rigid structure 120 (towards the acoustic sensor 110), and an inside end 455 facing towards the inside of the rigid structure 120.

In addition, the ball 452 is fastened to the transmission cable 140 and is positioned inside the ball support 451. In an example, the ball 452 has a through orifice with the transmission cable 140 passing through the orifice. In another example, the transmission cable 140 is fastened to the outside surface of the ball 451.

Thus, the connection means 450 enable the acoustic sensor 110 to perform movement in rotation R1 relative to the rigid structure 120. More precisely, the acoustic sensor 110 can move in rotation R1 with three degrees of freedom in rotation, this movement in rotation R1 being made possible by the ball 452 and the ball support 451. Nevertheless, such movement in rotation R1 is limited to a predetermined angle α1 relative to the surface of the rigid structure 120 by the outside wall 423 of the rigid structure 120 and the surface of the acoustic sensor 110 and/or the outside end edge 454 of the orifice 453 in the ball support 451. This movement in rotation R1 is thus limited for two degrees of freedom in rotation by the rigid structure.

Thus, when pressure is exerted on the outside wall 432 of the acoustic sensor 110, the acoustic sensor 110 can tilt, taking with it the transmission cable 140 and thus the ball 452. The acoustic sensor 110 is then oriented along the normal to the user's body at the point of contact between the acoustic sensor 110 and said body.

In a variant, the acoustic sensor 110 is a wireless sensor. In this variant, the transmission cable 140 is replaced by a rod connected to the acoustic sensor 110 and passing through the orifice 422, so that the acoustic sensor 110 is positioned outside the rigid structure 120.

The ball 452 is then fastened to the rod. Thus, when pressure is exerted on the outside wall 432 of the acoustic sensor 110, the acoustic sensor 110 can tilt taking with it the rod and thus with the ball 452.

Figure 5:
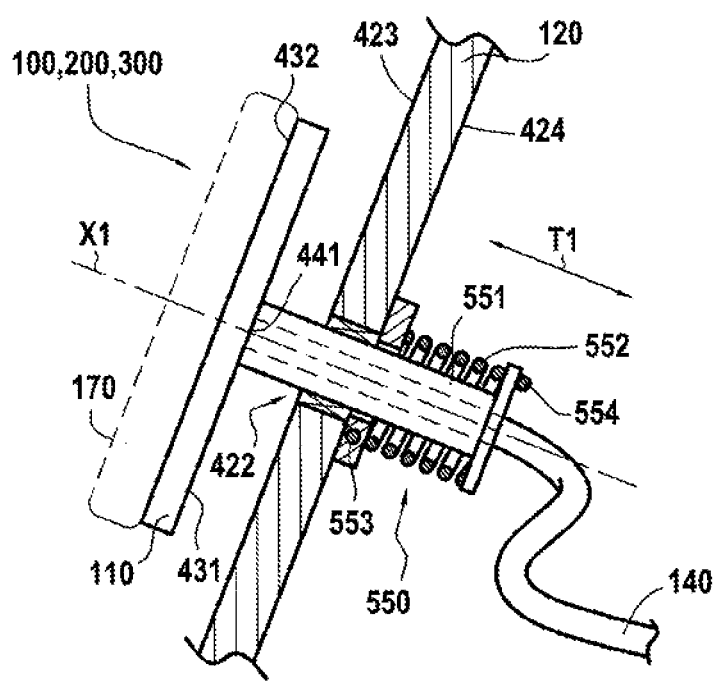

FIG. 5 schematically represents an acoustic sensor 110 connected to the rigid structure 120 via a second variant of the connection means 550 for the equipment 100, 200, 300, 1000, 1100 of the first, second, third, or fourth embodiment.

As in the first variant, the acoustic sensor 110 has an inside wall 431 facing towards the rigid structure 120, and an outside wall 432 facing the other way. The transmission cable 140 has a first end 441 fastened to the inside wall 431 of the acoustic sensor 110.

Furthermore, as in the first variant, the rigid structure 120 includes an orifice 422. This orifice 422 passes the transmission cable 140 so that the acoustic sensor 110 is positioned outside the rigid structure 120. The rigid structure 120 also includes an outside wall 423 facing towards the acoustic sensor 110, and an inside wall 424 facing the other way. In addition, the transmission cable 140 can slide in the orifice 422.

The connection means 550 comprise a rigid envelope 551 (or cable passage 551) and a spring 552. The rigid envelope 551 is fastened to the transmission cable 140 and surrounds a portion of the transmission cable 140 from the first end 441 of the transmission cable 140.

The spring 552 has a first end 553 and a second end 554. The first end 553 of the spring 552 is fastened to the inside wall 424 of the rigid structure 120. Furthermore, the second end 554 of the spring 552 is fastened on the rigid envelope 551. In a variant, the first end 553 of the spring 552 is positioned against the inside wall 431 of the acoustic sensor 110, and the second end 554 of the spring 252 is positioned against the outside wall 423 of the rigid structure 120.

Thus, the connection means 550 enable the acoustic sensor 110 to move in translation T1 relative to the rigid structure 120. More precisely, the acoustic sensor 110 can move in translation T1 along an axis X1 perpendicular to the outside wall 432 of the acoustic sensor 110 and passing through the orifice 422, this movement in translation T1 being limited by the surface of the rigid structure 120. In addition, the connection means 550 enable the acoustic sensor 110 to exert pressure against the subject's body when the equipment 100, 200, 300, 1000, or 1100 is positioned against the subject's body.

Thus, when pressure is exerted on the outside wall 432 of the acoustic sensor 110, the acoustic sensor 110 moves in translation T1 towards the rigid structure 120, taking with it the transmission cable 140, the rigid envelope 551, and thus the spring 552. Under normal situations of use of the equipment 100, 200, 300, 1000, or 1100, this movement in translation T1 serves to guarantee continuous contact between the acoustic sensor 110 and the subject's body.

In a variant, the acoustic sensor 110 is a wireless sensor. In this variant, the transmission cable 140 and the rigid envelope 551 are replaced by a rod connected to the acoustic sensor 110 and passing through the orifice 422 in such a manner that the acoustic sensor 110 is positioned outside the rigid structure 120.

The second end 554 of the spring 552 can then be fastened to the rod connected to the acoustic sensor 110. Thus, when pressure is exerted on the outside wall 432 of the acoustic sensor 110, the acoustic sensor 110 moves in translation T1 towards the rigid structure 120, taking with it the rod and thus the spring 552.

Figure 6:
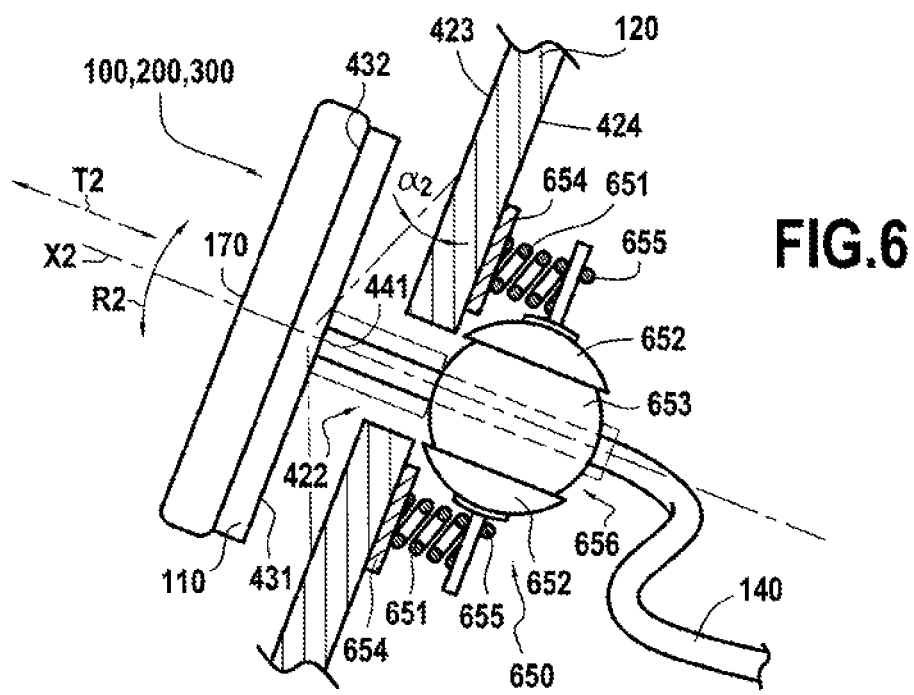

FIG. 6 schematically represents an acoustic sensor 110 connected to the rigid structure 120 via a third variant of the connection means 650 for the equipment 100, 200, 300, 1000, 1100 of the first, second, third, or fourth embodiment.

As in the first variant, the acoustic sensor 110 has an inside wall 431 facing towards the rigid structure 120, and an outside wall 432 facing the other way. The transmission cable 140 has a first end 441 connected to the inside wall 431 of the acoustic sensor 110.

Furthermore, as in the first variant, the rigid structure 120 includes an orifice 422. This orifice 422 passes the transmission cable 140 so that the acoustic sensor 110 is positioned outside the rigid structure 120. The rigid structure 120 also includes an outside wall 423 facing towards the acoustic sensor 110 and an inside wall 424 facing the other way. In addition, the transmission cable 140 can slide in the orifice 422.

The connection means 650 comprise two springs 651, a ball 653, and a ball support 652. In a variant, the connection means 650 include a number of springs 651 other than two.

Each spring 651 has a first end 654 and a second end 655. The first end 654 of each spring 651 is fastened to the inside wall 424 of the rigid structure 120. In an example, the two first ends 654 are positioned on a line passing through the center of the orifice 422 of the rigid structure 120.

The ball support 652 is fastened to the second end 655 of each of the springs 651. By way of example, the ball support 652 is in the form of a hollow sphere including a through orifice 656.

In addition, the ball 653 is fastened to the transmission cable 140 and is positioned inside the ball support 652. In an example, the ball 653 has a through orifice, the transmission cable 140 passing through the orifice and being fastened thereto. In another example, the transmission cable 140 is fastened to the outside surface of the ball 652.

Thus, the connection means 650 enable the acoustic sensor 110 to perform movement in rotation R2 and/or translation movement T2 relative to the rigid structure 120. More precisely, the acoustic sensor 110 can perform movement in rotation R2 with three degrees of freedom in rotation, this movement in rotation R2 being made possible by the ball 653 and the ball support 652. Nevertheless, this movement in rotation R2 is limited to a predetermined angle α2 relative to the surface of the rigid structure 120, by the outside wall 423 of the rigid structure 120 and the surface of the acoustic sensor 110 and/or the outside end edge of the orifice 656 of the ball support 652 and/or the outside end edge of the orifice 422 of the rigid structure 120. This movement in rotation R2 is thus limited for two degrees of freedom in rotation by the rigid structure 120.

In addition, the acoustic sensor 110 can move in translation T2 along an axis X2 perpendicular to the outside wall 432 of the acoustic sensor 110 and passing through the orifice 422, this movement in translation T2 being limited by the surface of the rigid structure 120.

Thus, when pressure is exerted against the outside wall 432 of the acoustic sensor 110, the acoustic sensor 110 moves in translation T2 and/or rotation R2 towards the rigid structure 120, and takes with it the transmission cable 140, the ball 653, and the ball support 652 for a movement in translation, or the transmission cable 140, the ball 653, the ball support 652, and the two springs 651 for a movement in rotation R2 or for a movement in translation T2 associated with a movement in translation R2. The acoustic sensor 110 is then oriented along the normal to the user's body at the point of contact between the acoustic sensor 110 and said body.

Furthermore, the connection means 650 enable the acoustic sensor 110 to exert pressure against the subject's body when the equipment 100, 200, 300, 1000, or 1100 is positioned against the subject's body. Under normal situations of use of the equipment 100, 200, 300, 1000, or 1100, this pressure serves to guarantee continuous contact between the acoustic sensor 110 and the subject's body.

The connection means 650 thus enable the acoustic sensor 110 to be oriented and to maintain contact between the acoustic sensor 110 and the user's body. The connection means 650 also enable the acoustic sensor 110 to exert sufficient pressure against the subject's body to enable high quality acoustic measurement to be performed.

In a variant, the acoustic sensor 110 is a wireless sensor. In this variant, the transmission cable 140 is replaced by a rod fastened to the acoustic sensor 110 and passing through the orifice 422, such that the acoustic sensor 110 is positioned outside the rigid structure 120.

The ball 653 is then fastened to the rod. Thus, when pressure is exerted against the outside wall 432 of the acoustic sensor HQ, the acoustic sensor 110 performs a movement in translation T2 and/or in rotation R2 towards the rigid structure 120, taking with it the rod, the ball 653, and the ball support 652 for a movement in translation, or the rod, the ball 653, the ball support 652, and the two springs 651 for a movement in rotation R2 or for a movement in translation T2 associated with a movement in rotation R2.

Figure 7:
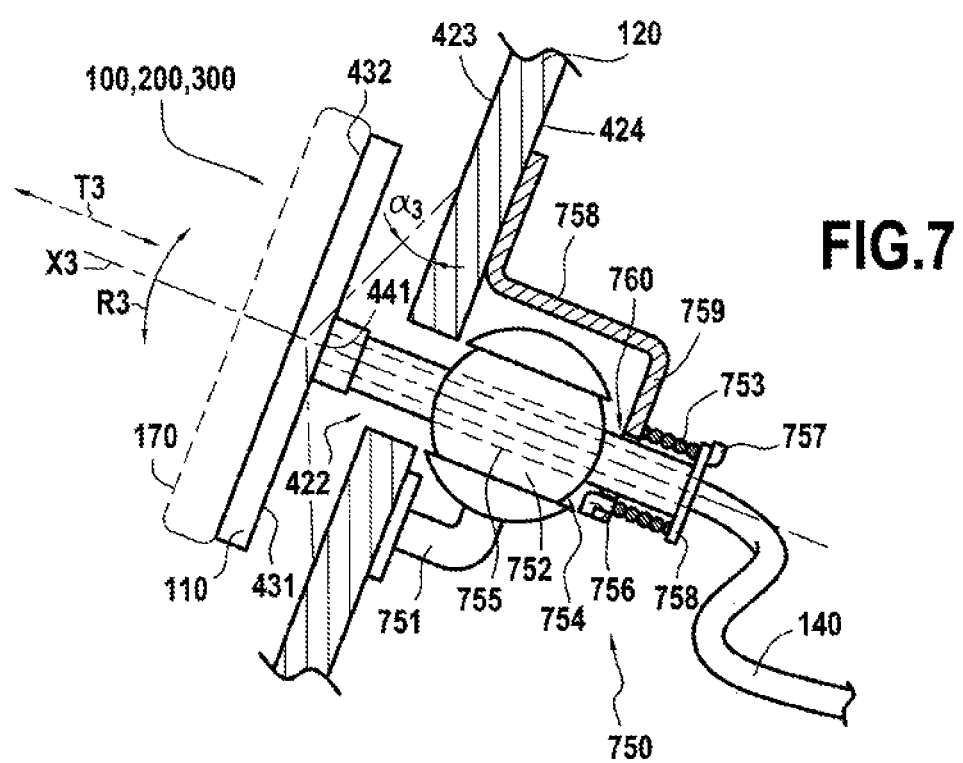

FIG. 7 schematically represents an acoustic sensor 110 connected to the rigid structure 120 via a fourth variant of the connection means 750 for the equipment 100, 200, 300, 1000, 1100 in the first, second, third, or fourth embodiment.

As in the first variant, the acoustic sensor 110 has an inside wall 431 facing towards the rigid structure 120 and an outside wall 432 facing the other way. The transmission cable 140 has a first end 441 fastened to the inside wall 431 of the acoustic sensor 110.

Furthermore, as in the first variant, the rigid structure 120 includes an orifice 422. This orifice 422 passes the transmission cable 140, such that the acoustic sensor 110 is positioned outside the rigid structure 120. The rigid structure 120 also includes an outside wall 423 facing towards the acoustic sensor 110 and an inside wall 424 facing the other way. In addition, the transmission cable 140 can slide in the orifice 422.

The connection means 750 comprise a ball 752, a ball support 751, a spring 753, and a spring support 758.

The ball support 751 is fastened to the inside wall 424 of the rigid structure 120. By way of example, the ball support 751 is in the form of a hollow sphere including a through orifice 754.

Furthermore, the ball 752 is fastened to the transmission cable 140 and is positioned inside the ball support 751. In an example, the ball 752 has a through orifice 755, with the transmission cable 140 passing therethrough and being capable of sliding through the orifice 755.

The spring support 758 is fastened to the inside wall 424 of the rigid structure 120. The spring support 758 includes a plate 759 having a through orifice 760, with the transmission cable 140 passing through the orifice 760 and being capable of sliding relative thereto. The diameter of the orifice 760 is large enough to enable the transmission cable 140 to perform movements in rotation relative to the plane of the plate 759 of the spring support 758. In a variant, the spring support 758 is fastened to the ball support 751.

The spring 753 has a first end 756 and a second end 757. The first end 756 of the spring 753 is fastened to the plate 759 of the spring support 758. The second end 757 of the spring 753 is fastened on stop means 758, the stop means 758 being fastened to the transmission cable 140. In a variant, the second end 757 of the spring 753 is fastened directly to the transmission cable 140. In an example, the spring 753 surrounds a portion of the transmission cable 140. In an example, a portion of the transmission cable 140 that extends through the acoustic sensor 110 at the second end 757 of the spring 753 is made rigid.

Thus, the connection means 750 enable the acoustic sensor 110 to perform movement in rotation R3 and/or in translation T3 relative to the rigid structure 120. More precisely, the acoustic sensor 110 can perform movement in rotation R3 with three degrees of freedom in rotation, this movement in rotation R3 being made possible by the ball 752 and the ball support 751. Nevertheless, this movement in rotation R3 is limited to a predetermined angle α3 relative to the surface of the rigid structure 120 by the outside wall portion 423 of the rigid structure 120 and the surface of the acoustic sensor 110 and/or the outside end edge of the orifice 754 of the ball support 751 and/or the outside end edge of the orifice 422 of the rigid structure 120. This movement in rotation R3 is thus limited for two degrees of freedom in rotation by the rigid structure 120.

In addition, the acoustic sensor 110 may move in translation T3 along an axis X3 perpendicular to the outside wall 432 of the acoustic sensor 110 and passing through the orifice 422, this movement in translation T3 being limited by the surface of the rigid structure 120.

Thus, when pressure is exerted against the outside wall 432 of the acoustic sensor 110, the acoustic sensor 110 moves in translation T3 and/or rotation R3 towards the rigid structure 120, taking with it the transmission cable 140 and the spring 753 for a movement in translation T3, or the transmission cable 140, the spring 753, and the ball 752 for a movement in rotation R3 or for a movement in translation T3 associated with a movement in rotation R3. The acoustic sensor 110 is then oriented along the normal to the user's body at the point of contact between the acoustic sensor 110 and said body.

Furthermore, the connection means 750 enable the acoustic sensor 110 to exert pressure against the subject's body when the equipment 100, 200, 300, 1000, or 1100 is positioned against the subject's body. Under normal conditions of use of the equipment 100, 200, 300, 1000, or 1100, this pressure makes it possible to guarantee continuous contact between the acoustic sensor 110 and the subject's body.

The connection means 750 thus enable the acoustic sensor 110 to be oriented and contact to be maintained between the acoustic sensor 110 and the user's body. The connection means 750 also make it possible for the acoustic sensor 110 to exert sufficient pressure against the subject's body to enable high quality acoustic measurement to be performed.

In a variant, the acoustic sensor 110 is a wireless sensor. In this variant, the transmission cable 140 is replaced by a rod connected to the acoustic sensor 110 and passing through the orifice 422, such that the acoustic sensor 110 is positioned outside the rigid structure 120.

The ball 752 is then connected to the rod and the rod passes through the orifice 760 and can slide relative thereto. In addition, the stop means 758 are fastened to the rod. In a variant, the second end 757 of the spring 753 is fastened directly to the rod. Furthermore, the spring 753 can surround a portion of the rod.

Thus, when pressure is exerted on the outside wall 432 of the acoustic sensor 110, the acoustic sensor 110 moves in translation T3 and/or in rotation R3 towards the rigid structure 120, taking with it the rod and the spring 753 for a movement in translation T3, or the rod, the spring 753, and the ball 752 for a movement in translation R3 or for a movement in translation T3 associated with a movement in rotation R3.

Figure 8:
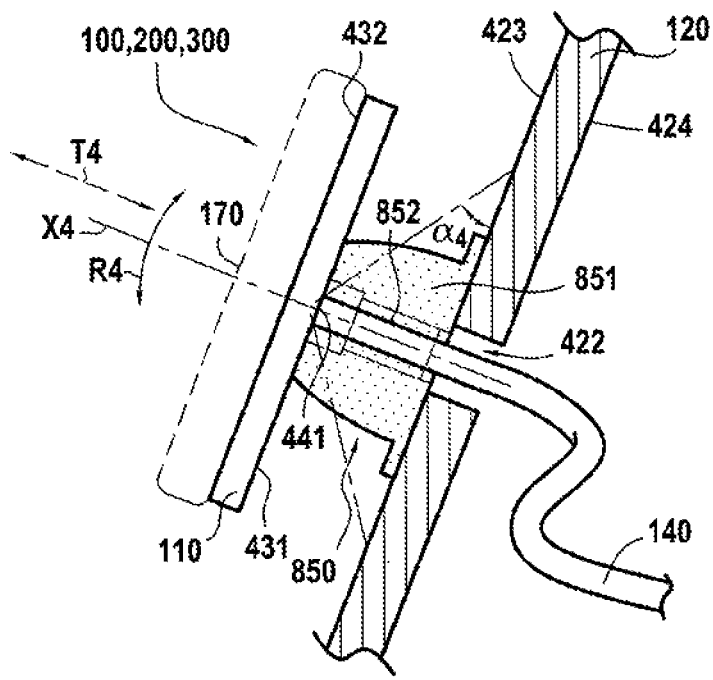

FIG. 8 schematically represents an acoustic sensor 110 connected to the rigid structure 120 via a fifth variant of the connection means 850 for the equipment 100, 200, 300, 1000, 1100 in the first, second, third, or fourth embodiment.

As in the first variant, the acoustic sensor 110 has an inside wall 431 facing towards the rigid structure 120, and an outside wall 432 facing the other way. The transmission cable 140 has a first end 441 fastened to the inside wall 431 of the acoustic sensor 110.

Furthermore, as in the first variant, the rigid structure 120 includes an orifice 422. This orifice 422 passes the transmission cable 140, such that the acoustic sensor 110 is positioned outside the rigid structure 120. The rigid structure 120 also has an outside wall 423 facing towards the acoustic sensor 110 and an inside wall 424 facing the other way. In addition, the transmission cable 140 can slide in the orifice 422.

The connection means 850 include a bellows 851 having an orifice 852 through which the transmission cable 140 passes. The bellows 851 is positioned between the acoustic sensor 110 and the rigid structure 120. The material of the bellows 851 enables the bellows 851 to be deformed when pressure is exerted on the bellows 851, and also enables the bellows 851 to return to its initial shape once the pressure is no longer exerted on the bellows 851. In an example, the bellows 851 is made of a material of the flexible plastics type.

Thus, the connection means 850 enable the acoustic sensor 110 to perform a movement in rotation R4 and/or in translation T4 relative to the rigid structure 120. More precisely, the acoustic sensor 110 may perform a movement in rotation R4 with three degrees of freedom in rotation, this movement in rotation R4 being made possible by the bellows 851. Nevertheless, this movement in rotation R4 is limited to a predetermined angle α4 relative to the surface of the rigid structure 120 by the outside wall 423 of the rigid structure 120 and by the surface of the acoustic sensor 110. This movement in rotation R4 is thus limited for two degrees of freedom in rotation by the rigid structure 120.

In addition, the acoustic sensor 110 can move in translation T4 along an axis X4 perpendicular to the outside wall 432 of the acoustic sensor 110 and passing through the orifice 422, this movement in translation T4 being limited by the surface of the rigid structure 120.

Thus, when pressure is exerted against the outside wall 432 of the acoustic sensor 110, the acoustic sensor 110 moves in translation T4 and/or in rotation R4 towards the rigid structure 120, and compresses the bellows 851. The acoustic sensor 110 is then oriented along the normal to the user's body at the point of contact between the acoustic sensor 110 and said body.

In addition, the connection means 850 enable the acoustic sensor 110 to exert pressure against the subject's body when the equipment 100, 200, 300, 1000, or 1100 is positioned against the subject's body. Under normal situations of use of the equipment 100, 200, 300, 1000, or 1100, this pressure makes it possible to guarantee continuous contact between the acoustic sensor 110 and the subject's body.

The connection means 850 thus make it possible to orient the acoustic sensor 110 and maintain contact between the acoustic sensor 110 and the user's body. The connection means 850 also enable the acoustic sensor 110 to exert sufficient pressure against the subject's body to enable high quality acoustic measurement to be performed.

In a variant, the acoustic sensor 110 is a wireless sensor. In this variant, the measurement device 105 does not have the transmission cable 140, the orifice 852, or the orifice 422.

Figure 9:
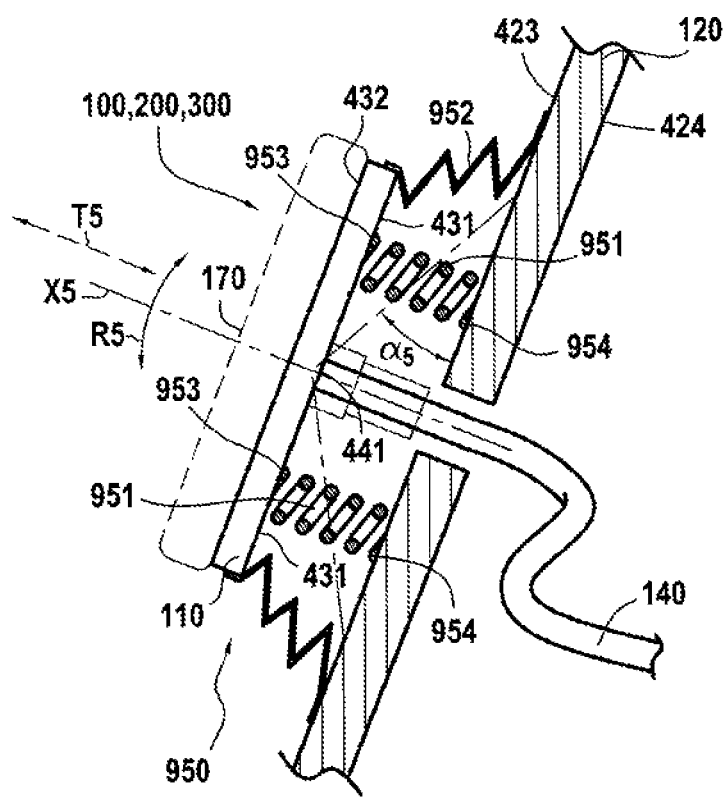

FIG. 9 schematically represents an acoustic sensor 110 connected to the rigid structure 120 via a sixth variant of the connection means 950 for equipment 100, 200, 300, 1000, 1100 in the first, second, third, or fourth embodiment.

As in the first variant, the acoustic sensor 110 has an inside wall 431 facing towards the rigid structure 120 and an outside wall 432 facing the other way. The transmission cable 140 has a first end 441 connected to the inside wall 431 of the acoustic sensor 110.

Furthermore, as in the first variant, the rigid structure 120 has an orifice 422. This orifice 422 passes the transmission cable 140 so that the acoustic sensor 110 is positioned outside the rigid structure 120. The rigid structure 120 further includes an outside wall 423 facing towards the acoustic sensor 110 and an inside wall 424 facing the other way. In addition, the transmission cable 140 can slide in the orifice 422.

The connection means 950 include two springs 951 and a flexible protective membrane 952. In a variant, the connection means 950 have a number of springs 951 other than two.

Each spring 951 has a first end 953 and a second end 954. The first end 953 is fastened to the inside wall 431 of the acoustic sensor 110. In addition, the second end 954 is fastened to the outside wall 423 of the rigid structure 120. In an example, the two second ends 954 are positioned on a line passing through the center of the orifice 422 of the rigid structure 120.

The flexible protective membrane 952 extends between the acoustic sensor 110 and the rigid structure 120. This flexible protective membrane 952 also extends all along the edge of the acoustic sensor 110.

Thus, the connection means 950 enable the acoustic sensor 110 to move in rotation R5 and/or in translation T5 relative to the rigid structure 120. More precisely, the acoustic sensor 110 can move in rotation R5 with three degrees of freedom in rotation, this movement in rotation R5 being made possible by the springs 951 and the flexible protective membrane 952. Nevertheless, this movement in rotation R5 is limited by a predetermined angle α5 relative to the surface of the rigid structure 120 by the outside wall 423 of the rigid structure 120 and the surface of the acoustic sensor 110. This movement in rotation R5 is thus limited for two degrees of freedom in rotation by the rigid structure 120.

In addition, the acoustic sensor 110 can move in translation T5 along an axis X5 perpendicular to the outside wall 432 of the acoustic sensor 110 and passing through the orifice 422, this movement in translation T5 being limited by the surface of the rigid structure 120.

Thus, when pressure is exerted against the outside wall 432 of the acoustic sensor 110, the acoustic sensor 110 moves in translation T5 and/or in rotation R5 towards the rigid structure 120, compressing the springs 951 and the flexible protective membrane 952. The acoustic sensor 110 is then oriented along the normal to the user's body at the point of contact between the acoustic sensor 110 and said body.

Furthermore, the connection means 950 enable the acoustic sensor 110 to exert pressure against the subject's body when the equipment 100, 200, 300, 1000, or 1100 is positioned against the subject's body. Under normal conditions of use of the equipment 100, 200, 300, 1000, or 1100, this pressure enables continuous contact to be guaranteed between the acoustic sensor 110 and the subject's body.

The connection means 950 thus enable the acoustic sensor 110 to be oriented and contact to be maintained between the acoustic sensor 110 and the user's body. The connection means 950 also enable the acoustic sensor 110 to exert sufficient pressure against the subject's body to enable high quality acoustic measurement to be performed.

In a variant, the acoustic sensor 110 is a wireless sensor. In this variant, the measurement device 105 does not have the transmission cable 140 or the orifice 422.

In the first, second, third, and fourth embodiments, the connection means 450, 550, 650, 750, 850, 950 may differ depending on the positions of the acoustic sensors 110 associated with the connection means 450, 550, 650, 750, 850, 950. It is thus possible to find connection means 450, 550, 650, 750, 850, 950 in accordance with a plurality of the above-described variants in the same piece of equipment 100, 200, 300, 1000, or 1100. In an example in which the user's body is substantially parallel to a central portion of the rigid structure 120 and presents a predetermined angle relative to a peripheral portion of the rigid structure 120 while the equipment 100, 200, 300, 1000, 1100 is in use, then connection means 550 in accordance with the second variant are associated with the acoustic sensors 110 positioned on the central portion, while connection means 450 in accordance with the first variant are associated with the acoustic sensors 110 positioned in the peripheral portion, so that these acoustic sensors c an be turned towards the user's body.

In an embodiment, the equipment 100, 200, 300, 1000, or 1100 is positioned in a health booth.

The invention claimed is:

1. Equipment to be positioned against the body of a subject, the equipment including an acoustic measurement device having:
    at least one acoustic sensor that measures for measuring acoustic signals given off by the subject's body, the at least one acoustic sensor includes a first outside wall that faces the subject and a first inside wall;
    a rigid structure, the rigid structure includes an orifice that extends through the rigid structure, and a second outside wall that faces the first inside wall of the at least one acoustic sensor;
    in a cross-sectional side view, an axis of the orifice intersects a center of the at least one acoustic sensor;
    connection means that connects the at least one acoustic sensor to the rigid structure in such a manner that the connection means and the at least one acoustic sensor are movable relative to the rigid structure and the connection means defining predetermined degrees of freedom of movement for the at least one acoustic sensor relative to the rigid structure; and
    an element attached to the first inside wall of the at least one acoustic sensor, the element extending toward the rigid structure and through the orifice, and the at least one acoustic sensor is positioned entirely outside the orifice.

2. Equipment according to claim 1, wherein, for at least one predetermined degree of freedom, the movement of the at least one acoustic sensor is limited by the second outside wall of the rigid structure.

3. Equipment according to claim 2, wherein the movement of the at least one acoustic sensor is limited in rotation by a predetermined angle relative to the second outside wall of the rigid structure and/or in translation along a predetermined linear shift towards the rigid structure.

4. Equipment according to claim 1, wherein the connection means resiliently biases the at least one acoustic sensor in a direction away from the rigid structure.

5. Equipment according to claim 1, wherein the connection means comprise:
    a ball support fastened to the rigid structure; and
    a ball connected to the at least one acoustic sensor and positioned inside the ball support.

6. Equipment according to claim 1, wherein the connection means comprise:
    a spring having a first end positioned against the rigid structure and a second end fastened to the at least one acoustic sensor.

7. Equipment according to claim 1, wherein the connection means comprise:
    a spring having a first end and a second end;
    a ball support; and
    a ball positioned inside the ball support.

8. Equipment according to claim 7, wherein:
    the ball is fastened to the at least one acoustic sensor;
    the first end of the spring is fastened to the rigid structure; and
    the second end of the spring is fastened to the ball support.

9. Equipment according to claim 7, wherein:
    the ball has an orifice passing the element connected to the at least one acoustic sensor;
    the ball support is fastened to the rigid structure;
    the first end of the spring is fastened to the rigid structure; and
    the second end of the spring is fastened to the element connected to the at least one acoustic sensor.

10. Equipment according to claim 1, wherein the connection means comprise a bellows positioned between the at least one acoustic sensor and the rigid structure.

11. Equipment according to claim 1, wherein the connection means comprise:
    a spring having a first end connected to the at least one acoustic sensor and a second end connected to the rigid structure; and
    a flexible protective membrane extending between the at least one acoustic sensor and the rigid structure.

12. Equipment according to claim 1, further including shield means positioned around the at least one acoustic sensor.

13. Equipment according to claim 1, wherein the at least one acoustic sensor is a stethoscope chestpiece.

14. Equipment according to claim 1, being in the form of a seat, a belt, a vest, a seat cover, or a harness.

15. An acoustic measurement device that measures acoustic signals generated by a body of a subject, the acoustic measurement device comprising:
    a plurality of acoustic sensors each of which measures acoustic signals generated by the subject's body, each acoustic sensor includes a first outside wall that faces the subject and a first inside wall;
    a rigid structure that includes a plurality of orifices that extend therethrough, and each orifice is associated with one of the acoustic sensors; the rigid structure includes a second outside wall that faces the first inside walls of the acoustic sensors;
    each one of the acoustic sensors is positioned entirely outside of its associated orifice;
    mechanical connectors that connect the acoustic sensors to the rigid structure in such a manner that the acoustic sensors are movable relative to the rigid structure, and the mechanical connectors define predetermined degrees of freedom of movement for the acoustic sensors relative to the rigid structure.

16. The acoustic measurement device of claim 15, wherein an axis of each orifice intersects a center of the associated acoustic sensor.

17. The acoustic measurement device of claim 15, wherein each mechanical connector surrounds an axis of a corresponding one of the orifices.

18. The acoustic measurement device of claim 15, wherein the mechanical connectors resiliently bias the acoustic sensors in a direction away from the rigid structure.

\* \* \* \* \*